(12) United States Patent
Fleury et al.

(10) Patent No.: US 11,202,617 B2
(45) Date of Patent: Dec. 21, 2021

(54) SYSTEMS AND METHODS FOR BODY PASSAGE NAVIGATION AND VISUALIZATION

(71) Applicant: Boston Scientific Scimed, Inc., Maple Grove, MN (US)

(72) Inventors: Sean P. Fleury, Minneapolis, MN (US); Peter L. Dayton, Brookline, MA (US); Ryan V. Wales, Northborough, MA (US); Paul Smith, Smithfield, RI (US); Scott E. Brechbiel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 399 days.

(21) Appl. No.: 15/904,846

(22) Filed: Feb. 26, 2018

(65) Prior Publication Data

US 2018/0242948 A1 Aug. 30, 2018

Related U.S. Application Data

(60) Provisional application No. 62/464,166, filed on Feb. 27, 2017.

(51) Int. Cl.
*A61B 1/018* (2006.01)
*A61B 8/00* (2006.01)
(Continued)

(52) U.S. Cl.
CPC ........ *A61B 8/4455* (2013.01); *A61B 1/00089* (2013.01); *A61B 1/018* (2013.01); *A61B 8/085* (2013.01); *A61B 8/0841* (2013.01); *A61B 8/12* (2013.01); *A61B 10/0233* (2013.01); *A61B 10/04* (2013.01); *A61B 8/4461* (2013.01);
(Continued)

(58) Field of Classification Search
CPC ..... A61B 10/02; A61B 10/0233; A61B 10/04; A61B 1/00089; A61B 1/018; A61B 2010/045; A61B 2017/00292; A61B 2090/378; A61B 8/0841; A61B 8/085; A61B 8/12; A61B 8/4455; A61B 8/4461
See application file for complete search history.

(56) References Cited

U.S. PATENT DOCUMENTS 5,474,075 A 12/1995 Goldberg et al.
6,099,464 A 8/2000 Shimizu et al.
(Continued)

FOREIGN PATENT DOCUMENTS

CN 105101883 A 11/2015
JP 06063042 U 9/1994
(Continued)

OTHER PUBLICATIONS

International Search Report and Written Opinion dated May 28, 2018, for PCT/US18/19669 (11 pages).

*Primary Examiner* — Mark D Remaly
(74) *Attorney, Agent, or Firm* — Kacvinsky Daisak Bluni PLLC

(57) ABSTRACT

The present disclosure relates to systems and methods for enhanced navigation and visualization of body passages. In particular, the systems and methods of the present disclosure provide enhanced navigation through the pulmonary peripheries, and enhanced visualization within larger pulmonary passages.

17 Claims, 7 Drawing Sheets

(51) Int. Cl.
*A61B 8/12* (2006.01)
*A61B 1/00* (2006.01)
*A61B 10/02* (2006.01)
*A61B 8/08* (2006.01)
*A61B 10/04* (2006.01)
*A61B 90/00* (2016.01)
*A61B 17/00* (2006.01)

(52) U.S. Cl.
CPC ......... *A61B 10/02* (2013.01); *A61B 2010/045* (2013.01); *A61B 2017/00292* (2013.01); *A61B 2090/378* (2016.02)

(56) References Cited

U.S. PATENT DOCUMENTS

| | | | |
|---|---|---|---|
| 2007/0225559 | A1 | 9/2007 | Clerc et al. |
| 2008/0004528 | A1 | 1/2008 | Fitzsimons et al. |
| 2008/0015569 | A1* | 1/2008 | Saadat ................. A61B 5/6882 606/41 |
| 2011/0245679 | A1 | 10/2011 | Yamakita |
| 2013/0225997 | A1 | 8/2013 | Dillard et al. |
| 2013/0281844 | A1 | 10/2013 | Karino et al. |
| 2014/0213850 | A1* | 7/2014 | Levy ................... A61B 1/0615 600/156 |
| 2015/0313451 | A1* | 11/2015 | Salman ............. A61B 1/00098 600/153 |

FOREIGN PATENT DOCUMENTS

| | | |
|---|---|---|
| JP | H07136169 A | 5/1995 |
| JP | H08322843 A | 12/1996 |
| JP | 2001104315 A | 4/2001 |
| JP | 2006198162 A | 8/2006 |
| JP | 2010253174 | 11/2010 |
| JP | 2011212160 A | 10/2011 |
| WO | 2008008796 | 1/2008 |
| WO | 2015153931 | 10/2015 |

* cited by examiner

SYSTEMS AND METHODS FOR BODY PASSAGE NAVIGATION AND VISUALIZATION

CROSS REFERENCE TO RELATED APPLICATIONS

The present application claims the benefit of priority under 35 U.S.C. § 119 to U.S. Provisional Patent Application Ser. No. 62/464,166, filed on Feb. 27, 2017, which is incorporated by reference in its entirety for all purposes.

FIELD

The present disclosure relates to systems and methods for enhanced navigation through body passages and improved visualization and sampling of target tissue.

BACKGROUND

Navigation and visualization within body passages with ultrasound probes presents difficulties with preventing damage to the probes and optimizing visualization. For example, radial endobronchial ultrasound (R-EBUS) provides a minimally invasive option when clinical presentation indicates that tissue biopsy within the pulmonary system is necessary. The ultrasound component of such a pulmonary tissue biopsy system is critical for visualization of target nodules in the pulmonary passages. Ultrasound energy is only capable of propagating through materials, such as polymers, with a certain density and refraction index, thereby requiring the ultrasound probe to be extendible beyond the distal end of the delivery catheter. Due to the dimensional constraints of the pulmonary peripheries, the exposed portion of the ultrasound probe tends to be small and fragile and therefore susceptible to damage. The lack of a tapered/atraumatic leading edge on the exposed portion may allow even a moderate bump along the wall of the pulmonary passages to cause the ultrasound probe to kink and/or break, requiring the introduction of a new device to continue the procedure. In addition, visualization of target nodules within larger pulmonary passages tends to be impaired by the presence of open spaces (e.g., air) between the ultrasound probe and tissue wall, which blocks/attenuates propagation of the ultrasound signal.

Accordingly, various advantages may be realized by a system that allows enhanced navigation through narrow body passages and improved target tissue visualization within larger body passages.

SUMMARY

The present disclosure, in its various aspects, provides advantages in the medical field, such as the field of pulmonary endoscopy, of a sampling system that may allow enhanced navigation through body passages and improved visualization and sampling of target tissue. In various embodiments, the sampling system may include an endcap which protects the exposed portion of an ultrasound probe and enhances contact with the wall of the body passage and propagation of the ultrasound signal for improved target tissue visualization.

In one aspect, the present disclosure relates to a system comprising an elongate member which may include first and second working channels defining respective first and second openings. An ultrasound probe may be disposed within the first working channel such that a distal portion of the ultrasound probe is extendable distally beyond a distal end of the elongate member. An endcap may be attached to the distal end of the elongate member to enclose the distal portion of the ultrasound probe when the probe is extended outside of the first opening. A tissue sampling element may be slidably disposed within the second working channel. The first working channel may extend between a proximal end and a distal end of the elongate member to define the first opening. The second working channel may extend between a proximal end of the elongate member and an outer surface of the elongate member to define the second opening. The second working channel may define a ramped surface at the second opening within a distal portion of the elongate member. The endcap may include a hard plastic material. The endcap may be filled with a conductive material. The endcap may include an expandable member configured to move between a first configuration and a second configuration. The expandable member may be moveable from the first configuration to the second configuration by flowing an inflation fluid into an interior of the expandable member. The expandable member may be moveable from the second configuration to the first configuration by flowing the inflation fluid out of the interior region of the expandable member. The ultrasound probe may be fixed within the first working channel. The ultrasound probe may be slidable within the first working channel. The endcap may be attached to a circumference of the distal end of the elongate member. The endcap may be attached about (e.g., around) the first opening of the distal end of the elongate member.

In another aspect, the present disclosure relates to a system comprising an elongate member which may include first and second working channels defining respective first and second openings. An ultrasound probe may be disposed within the first working channel such that a distal portion of the ultrasound probe is extendable distally beyond a distal end of the elongate member. An endcap may be attached to the distal portion of the ultrasound probe. A tissue sampling element may be slidably disposed within the second working channel. The first working channel may extend between a proximal end and a distal end of the elongate member to define the first opening. The second working channel may extend between a proximal end of the elongate member and an outer surface of the elongate member to define the second opening. The second working channel may define a ramped surface at the second opening within a distal portion of the elongate member. The endcap may include an expandable member configured to move between a first configuration and a second configuration. The expandable member may be moveable from the first configuration to the second configuration by flowing an inflation fluid into an interior of the expandable member. The expandable member may be moveable from the second configuration to the first configuration by flowing the inflation fluid out of the interior region of the expandable member. The ultrasound probe may be fixed within the first working channel. The ultrasound probe may be slidable within the first working channel.

In another aspect, the present disclosure relates to a method comprising advancing a system into a body passage, wherein the system may include an elongate member, an ultrasound probe disposed within a first working channel of the elongate member, and an expandable member attached to a distal end of the elongate member. A distal portion of the ultrasound probe may extend distally beyond a distal end of the elongate member. The expandable member may be attached to the distal end of the elongate member to enclose the distal portion of the ultrasound probe. The expandable member may move from a first configuration to a second configuration to place the expandable member in contact with a wall of the body passage adjacent a target tissue. An ultrasound image of the body passage and/or target tissue may be obtained using the ultrasound probe. The expandable member may be advanced through the body passage in the second configuration. The method may further include advancing a tissue sampling element distally beyond the second opening into the target tissue such that a portion of the target tissue is captured within a lumen of the tissue sampling element. The system may be withdrawn from the body passage and the tissue sample captured within the lumen of the tissue sampling element analyzed.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 1A:
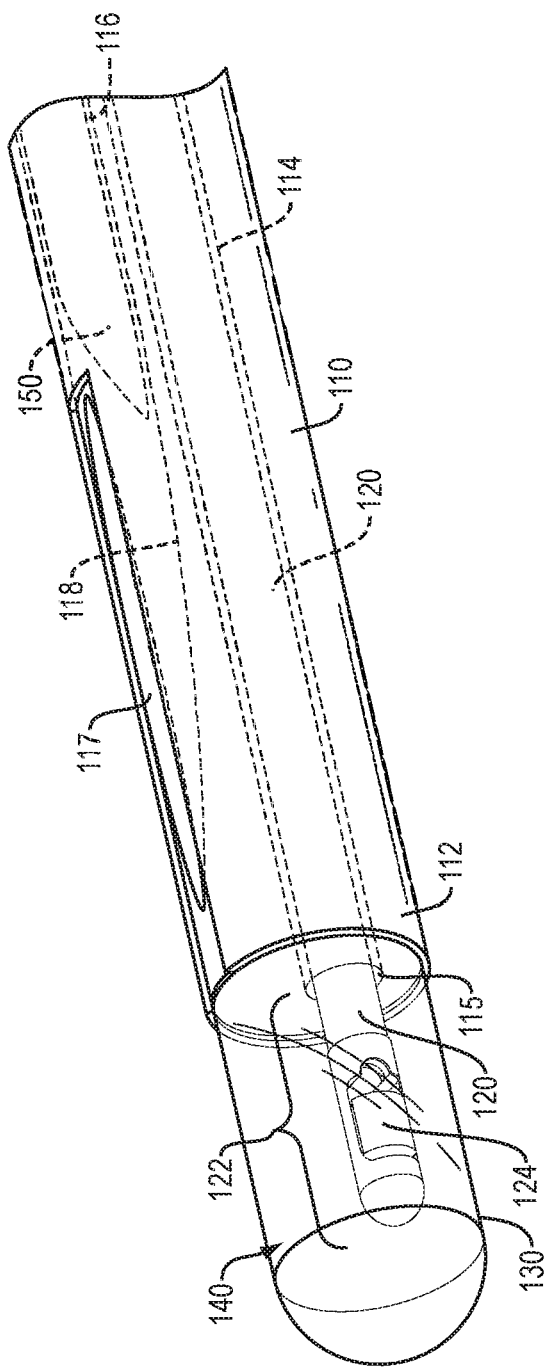
FIGS. 1A-1B provide a schematic view of a tissue biopsy system, according to one embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to enhanced navigation through pulmonary passages and improved visualization and sampling of pulmonary nodules, the systems and methods disclosed herein may be used to image and obtain biopsy samples from within a variety of body lumens, including, for example, the heart, vascular system, circulatory system, gastrointestinal (GI) tract, stomach, esophagus, urogenital system and the like. In various embodiments, the catheter endcap may be suitable for use with variety of tissue sampling tools (e.g., grasping or cutting elements) in addition to biopsy needles.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from a medical professional when introducing a device into a patient, while the term "proximal" refers to the end closest to the medical professional when introducing a device into a patient.

The present disclosure generally provides a tissue biopsy system for enhanced navigation and visualization of large and small body passages. In particular, the disclosed tissue biopsy systems generally include an elongate member with working channels to accommodate respective a tissue sampling element and an ultrasound probe, and an endcap configured to protect/support the exposed portion of the ultrasound probe and to maintain direct tissue wall contact with body passages of various sizes and/or shapes. In various embodiments, the ultrasound probe may be fixedly or slidably disposed within a first working channel of the elongate member. Additionally, a distal portion of the ultrasound probe, including the ultrasound transducer, may extend through a first opening, and distally beyond the distal end, of the elongate member.

Referring to FIG. 1A, in one embodiment, a tissue biopsy system of the present disclosure may include an elongate member 110 (e.g., catheter, delivery device, etc.) comprising first and second working channels 114, 116, which define respective first and second openings 115, 117. The first and second openings 115, 117 are not limited to substantially circular and oblong shapes, respectively, but may include a variety of other shapes and/or configurations. The first working channel 114 may extend between a proximal end (not shown) and distal end 112 of the elongate member 110 to define the first opening 115. The second working channel 116 may extend between the proximal end (not shown) and an outer surface 113 of the elongate member 110 to define the second opening 117. The second working channel 116 may form a sloped or ramped surface 118 at the second opening 117 within the distal portion of the elongate member 110. The ramped surface 118 may include an angle of approximately 5 degrees to approximately 10 degrees relative to a longitudinal axis of the elongate member 110, and may include any degree of angle therebetween. The second working channel 116 may be configured to slidably receive a tissue sampling element 150 (e.g., biopsy needle, etc.).

The first working channel 114 may be configured to receive an ultrasound probe 120 with an ultrasound transducer 124 rotationally disposed on a distal end thereof. In one embodiment, the ultrasound probe 120 may be fixedly disposed within the first working channel 114. In another embodiment, the ultrasound probe 120 may be slidably disposed within the first working channel. A distal portion 122 of the ultrasound probe 120, including the ultrasound transducer 124, may extend through the first opening 115 and distally beyond the distal end 112 of the elongate member 110.

Figure 1B:
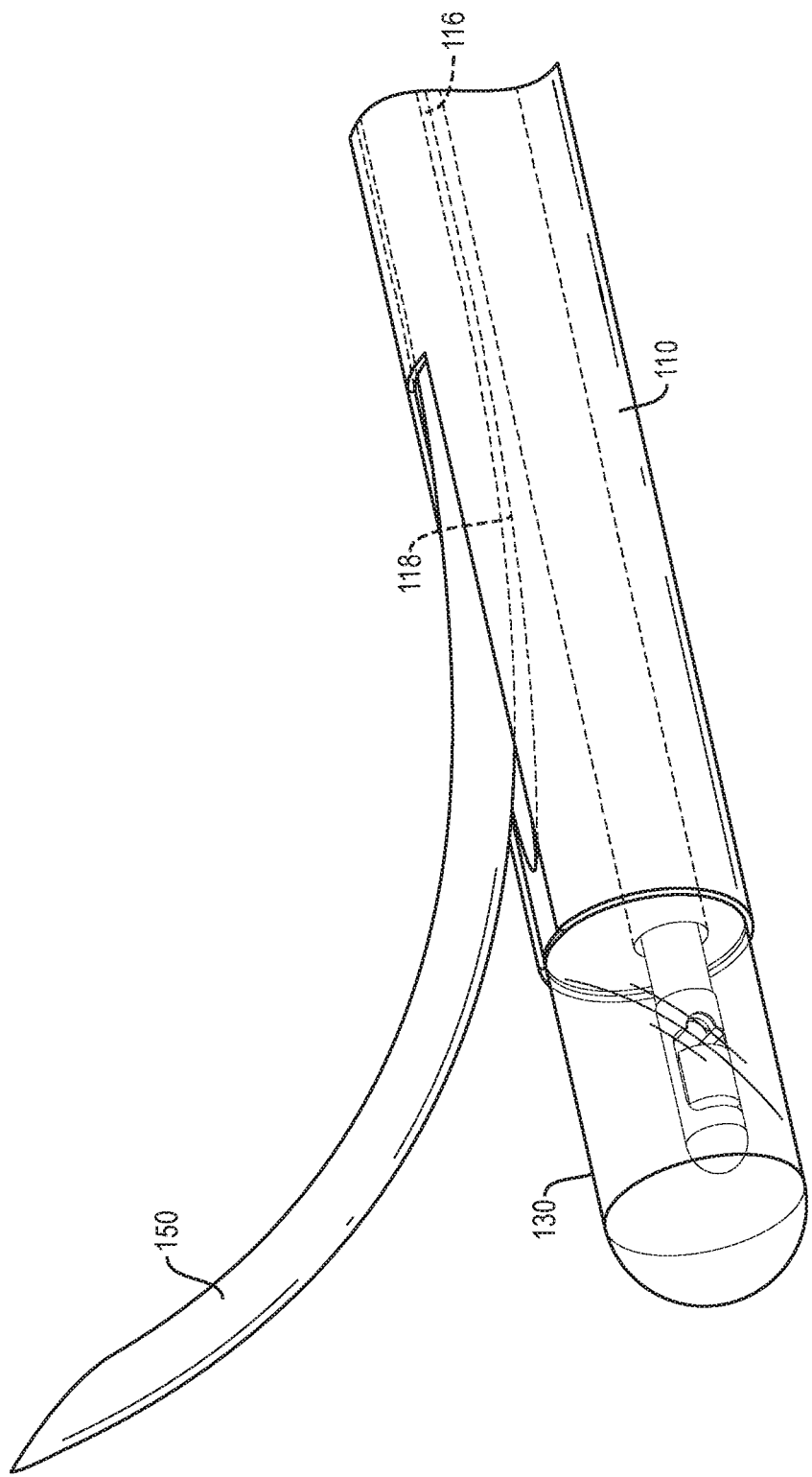

An endcap 130 may be attached to the distal end 112 of the elongate member 110 to enclose and protect the ultrasound transducer 124. In one embodiment, the endcap 130 may comprise a polymeric material, including, but not limited to, high density polyethylene (HDPE), with a suitable thickness and refractive index to allow unattenuated propagation of ultrasound energy therethrough. For example, the endcap 130 may include a hard plastic material with an atraumatic end (e.g. conical, bullet-like shape, etc.) to navigate through tortuous and narrow pulmonary passages. The endcap 130 may be permanently attached to the distal end 112 of the elongate member 110 by a suitable weld, solder, braze, adhesive, epoxy, glue and/or resin. In addition, or alternatively, the endcap 130 may be reversibly attached to the distal end 112 of the elongate member 110 by at least one of a snap-fit, press fit, interference fit and/or compressive fit. The endcap 130 may define an open (e.g., hollow) interior space which may be filled with a conductive material 140 (e.g., polyethylene glycol (PEG), petroleum gel, carbowax, saline, etc.) which eliminates the need to flush the ultrasound probe with saline throughout the course of a medical procedure. In embodiments in which the endcap 130 is reversibly attached to the elongate member 110, the endcap may be loaded or re-loaded with the conductive material immediately prior to use. The endcap 130 may include an outer diameter approximately equal to the outer diameter of the elongate member 110 to provide radial (e.g., 360 degree) contact with the tissue wall of a pulmonary passage. The ability of the endcap 130 to directly contact the complete inner circumference of larger pulmonary passages may provide an improved ultrasound image by removing empty spaces (e.g., air) which blocks/attenuates ultrasound energy from contacting/penetrating the tissue wall. In addition, the atraumatic profile and low friction outer surface may allow the endcap 130 to maintain full circumferential contact with the tissue wall as the tissue biopsy system is advanced into narrower pulmonary peripheries. Referring to FIG. 1B, the tissue sampling element 150 may be distally advanced along ramped surface 118 of the second working channel 116 such that the tissue sampling element 150 deflects (e.g., bends) away from a longitudinal axis of the elongate member 110 without contacting the endcap 130 upon exiting the second opening 117.

Figure 2A:
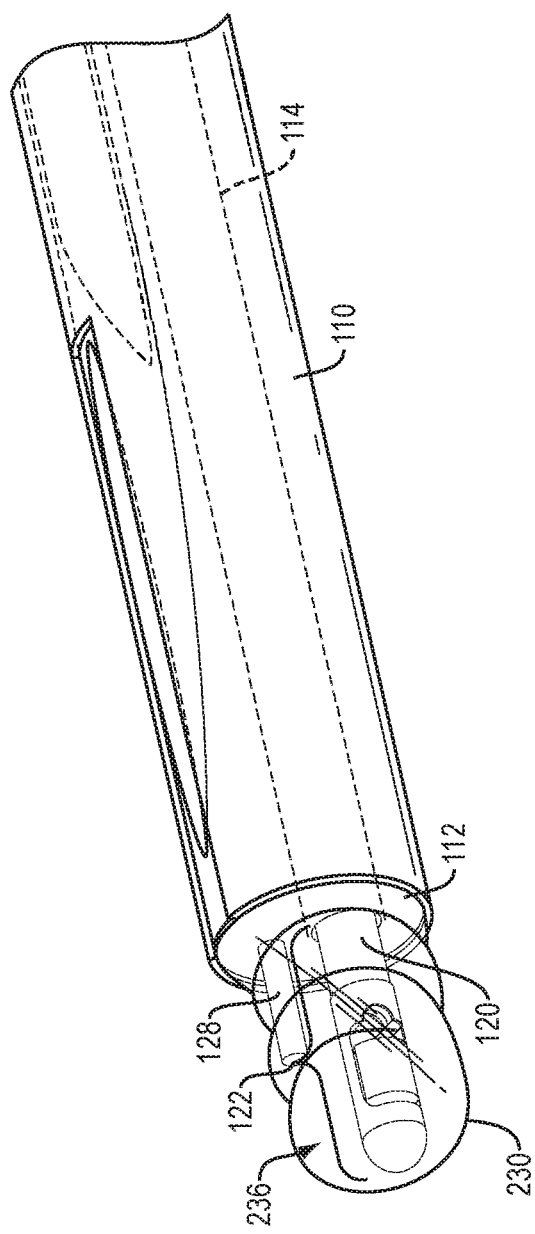
FIGS. 2A-2E provide a schematic view of a tissue biopsy system, according to another embodiment of the present disclosure.
Figure 2B:
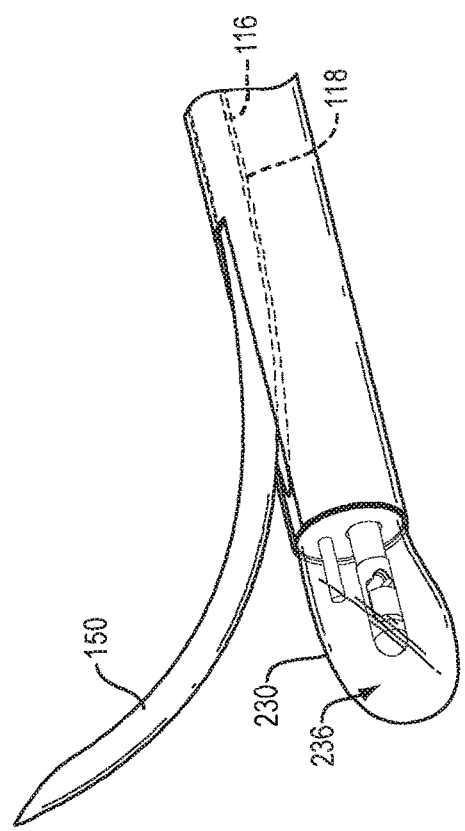
Figure 2C:
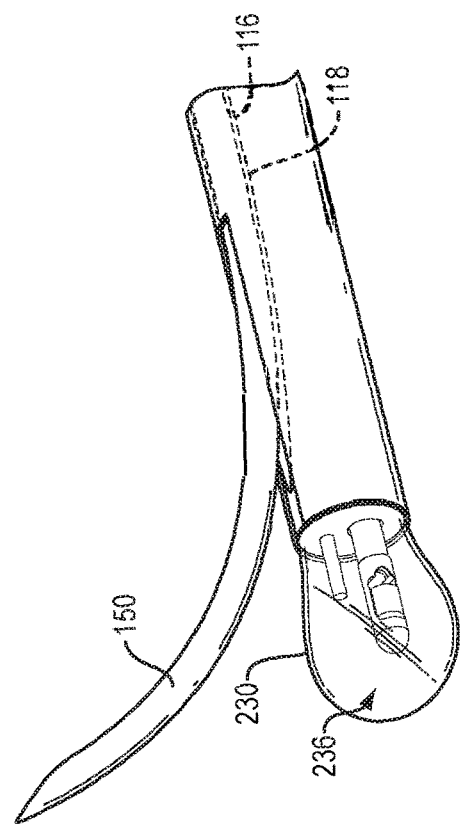
Figure 2D:
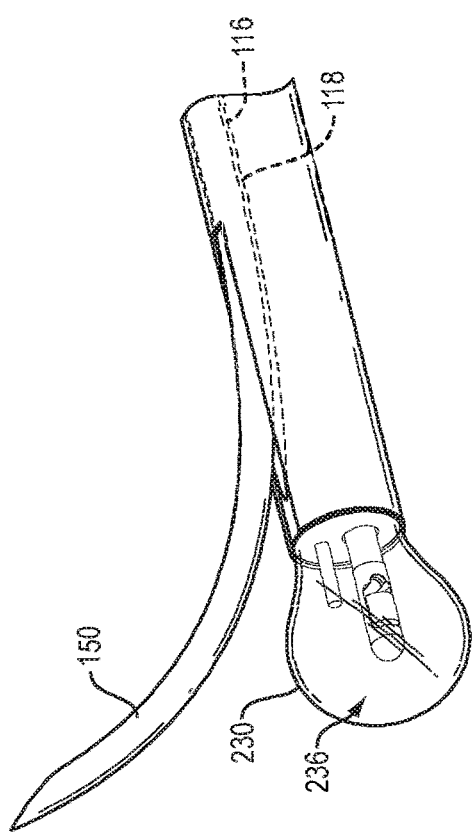
Figure 2E:
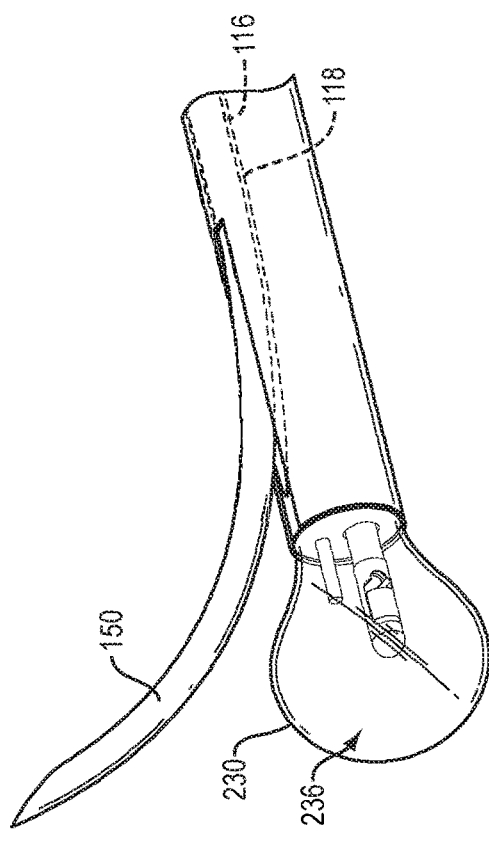

Referring to FIG. 2A, in one embodiment, the distal end 112 of the elongate member 110 may include an endcap 230 (e.g., expandable member, balloon, etc.) comprising one or more elastomeric and/or compliant materials with a suitable thickness and refractive index to allow unattenuated propagation of ultrasound energy therethrough. Semi-compliant materials may include, by way of non-limiting example, polyester elastomers (e.g., Amitel, Hytrel, etc.). Compliant materials may include, by way of non-limiting example, latex and silicone. As will be understood by those of skill in the art, an endcap formed from compliant materials may be capable of expanding indefinitely (e.g., does not have a fixed final diameter). For example, these materials may include compliances preferably in the range of 10% to 800%, and more preferably in the range of 50% to 200%. The endcap 230 may be permanently attached to the distal end 112 of the elongate member 110 by a suitable adhesive, epoxy, glue and/or resin. Alternatively, the endcap 230 may be reversibly attached to the distal end 112 of the elongate member 110 by at least one of a snap-fit, press fit, interference fit and/or compressive fit. The endcap 230 may be configured to move between a first configuration (e.g., collapsed, pre-inflated, etc.) and one or more second configurations (e.g., expanded, inflated, etc.) by flowing an inflation fluid (e.g., saline, gel, etc.) between an external fluid source (not shown) and an interior region 236 of the endcap. In one embodiment, the elongate member 110 may include a dedicated inflation fluid delivery lumen 128 extending between the proximal end (not shown) and distal end 112 to place the external fluid source and interior region 236 in fluid communication. Alternatively, the inflation fluid may flow between the external fluid source and the interior region 236 of the endcap 230 through the first working channel 114 of the elongate member 110 in the ancillary space around the ultrasound probe 120.

In the first configuration, the endcap 230 may fold or collapse around the distal portion 122 of the ultrasound probe 120 to provide a reduced profile (e.g., smaller diameter) such that the tissue biopsy system may pass through the working channel of a medical device (e.g., bronchoscope, etc.). In addition, the reduced profile of the endcap 230 may provide structural support to the distal portion 122 of the ultrasound probe 120 to prevent kinking and/or bending as the tissue biopsy system is advanced through the pulmonary passages.

An end cap with compliant or semi-compliant material(s) may allow the endcap 230 to move from the first configuration (FIG. 2A) to a variety of second configurations (FIGS. 2B-2E) depending on the specific dimensions of the pulmonary passage. With the tissue biopsy system positioned within a portion of the pulmonary passage to be visualized, inflation fluid may be introduced into the interior region 236 of the endcap 230 until the outer surface of the endcap 230 is placed in direct contact with the inner circumference of the pulmonary passage. Although FIGS. 2B-2E illustrate the endcap 230 as expanding in an approximately even or symmetrical configuration, the compliant or semi-compliant materials may allow the endcap 230 to expand asymmetrically to establish complete contact with irregular or unevenly shaped body passages (e.g., bifurcations, etc.). The atraumatic profile and low friction outer surface of the endcap 230 may maintain full circumferential contact with the tissue wall as the tissue biopsy system is advanced into narrower pulmonary peripheries. Inflation fluid may be introduced into, or removed from, the interior region 236 of the endcap 230 as necessary to maintain contact with the tissue walls of the pulmonary passages throughout the medical procedure. Regardless of the inflation level of the endcap 230, the tissue sampling element 150 may be distally advanced along ramped surface 118 of the second working channel 116 such that the tissue sampling element 150 deflects (e.g., bends) away from a longitudinal axis of the elongate member 110 without contacting the endcap 230 upon exiting the second opening 117.

In another embodiment, the endcap 230 may comprise one or more non-compliant materials configured to move from between a first configuration to a single/fixed diameter second configuration. Non-compliant materials may include, by way of non-limiting example, polyethylene terephthalate (PET). As compared to compliant or semi-compliant materials, non-compliant materials may provide increased structural support of the distal portion 122 of the ultrasound probe 120 when the endcap 230 is in the first configuration. The non-compliant materials may also provide increased structural support when in the second configuration, e.g., to better control the force exerted on the inner circumference of the pulmonary passage and/or resist puncturing due to unintended contact with the tissue sampling element 150.

Figure 3A:
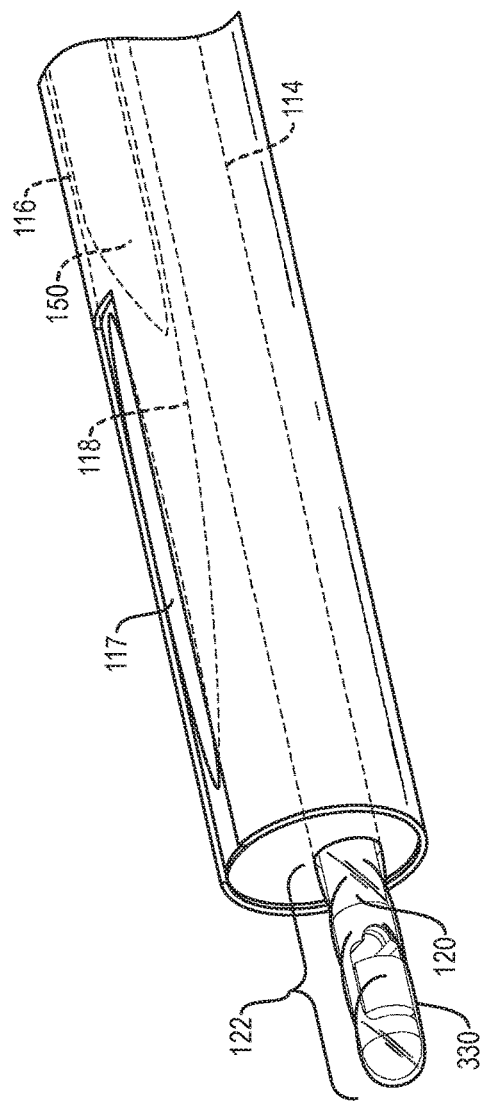
FIGS. 3A-3B provide a schematic view of a tissue biopsy system, according to another embodiment of the present disclosure.
Figure 3B:
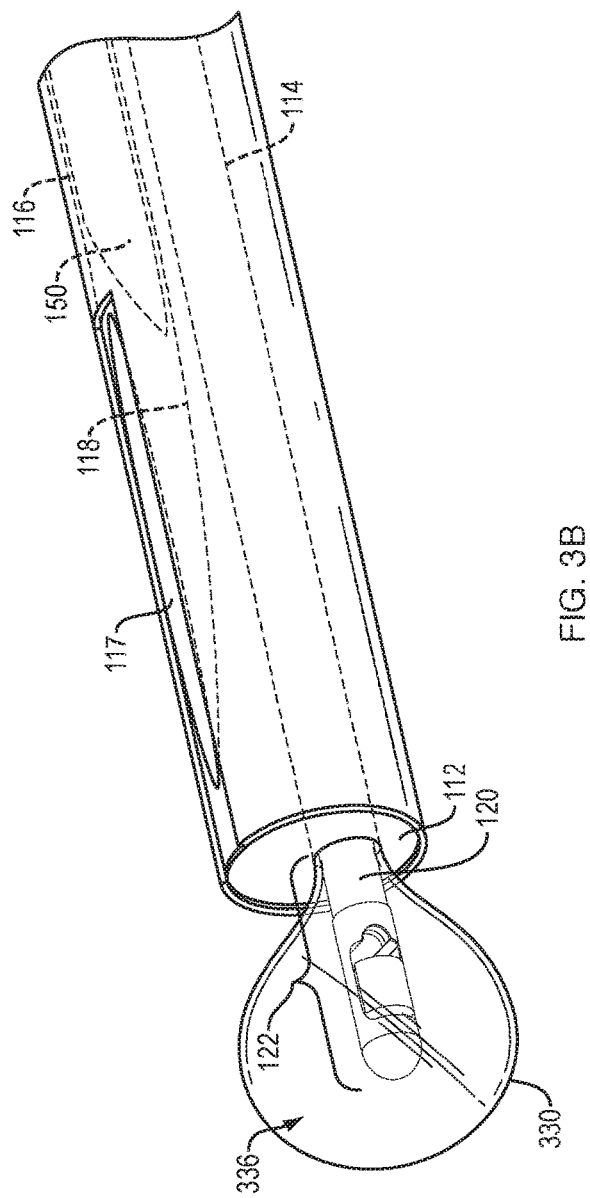

Referring to FIGS. 3A-3B, in another embodiment, a tissue biopsy system of the present disclosure may include an endcap 330 comprising a compliant, semi-compliant or non-compliant material attached to the distal portion 122 of the ultrasound probe 120. The endcap 330 may move between a first configuration (FIG. 3A) and a second configuration (FIG. 3B) by flowing an inflation fluid (e.g., saline, etc.) between an external fluid source (not shown)

and an interior region 336 of the endcap 330. For example, inflation fluid may flow between the external fluid source and the interior region 336 of the endcap 330 through a dedicated fluid delivery lumen (not shown) extending along or through the ultrasound probe 120. Alternatively, the endcap 330 may be attached to the distal end 112 of the elongate tubular member 110 around the first opening 115, such that inflation fluid may flow between the external fluid source and the interior region 336 of the endcap 330 through the first working channel 114 of the elongate member 110 in the ancillary space around the ultrasound probe 120. In the first configuration, the endcap 330 may fold or collapse around the distal portion 122 of the ultrasound probe 120 to provide a reduced profile (e.g., smaller diameter) such that the tissue biopsy system may pass through the working channel of a medical device (e.g., bronchoscope, etc.). In addition, the endcap 330 may provide structural support to the distal portion 122 of the ultrasound probe 120 to prevent kinking and/or bending as the tissue biopsy system is advanced through the pulmonary passages.

Once the tissue biopsy system is positioned within a portion of a pulmonary passage which the medical professional wishes to visualize, inflation fluid may be introduced into the interior region 336 of the endcap 330 until the outer surface of the endcap is placed in direct contact with the inner circumference of the pulmonary passage. As above, an endcap 330 comprising a compliant or semi compliant material may expand asymmetrically to establish complete contact with irregular or unevenly shaped body passages. The atraumatic profile and low friction outer surface of the endcap 330 may maintain full circumferential contact with the tissue wall as the tissue biopsy system is advanced into narrower pulmonary peripheries. Inflation fluid may be introduced into, or removed from, the interior region 336 of the endcap 330 as necessary to maintain contact with the tissue walls of the pulmonary passages throughout the medical procedure. Regardless of the inflation level of the endcap, the tissue sampling element 150 may be distally advanced along ramped surface 118 of the second working channel 116 such that the tissue sampling element 150 deflects (e.g., bends) away from a longitudinal axis of the elongate member 110 without contacting the endcap 330 upon exiting the second opening 117.

Figure 4A:
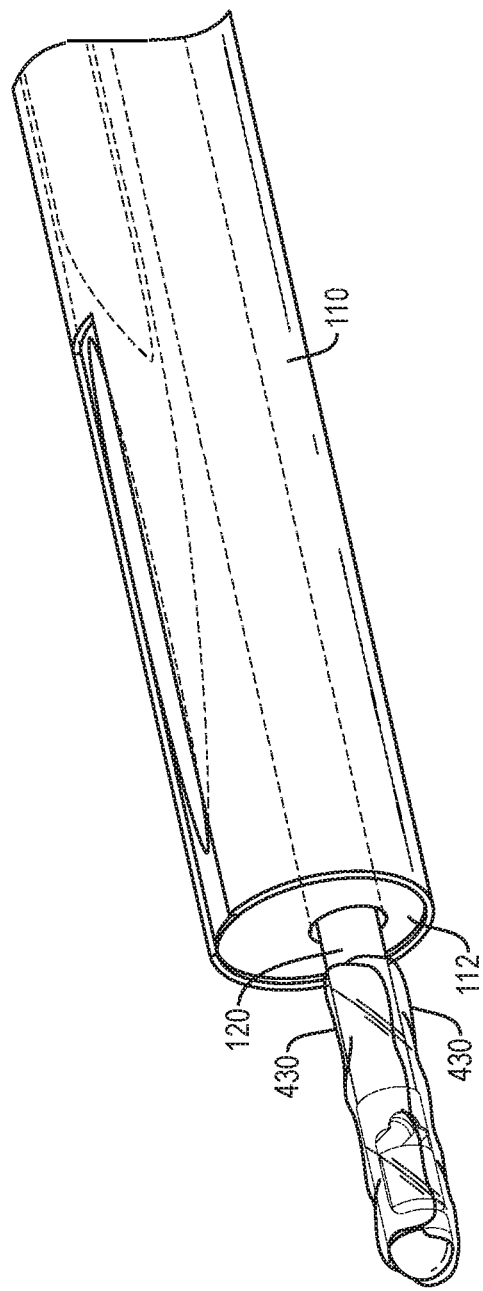
FIGS. 4A-4B provide a schematic view of a tissue biopsy system, according to another embodiment of the present disclosure.
Figure 4B:
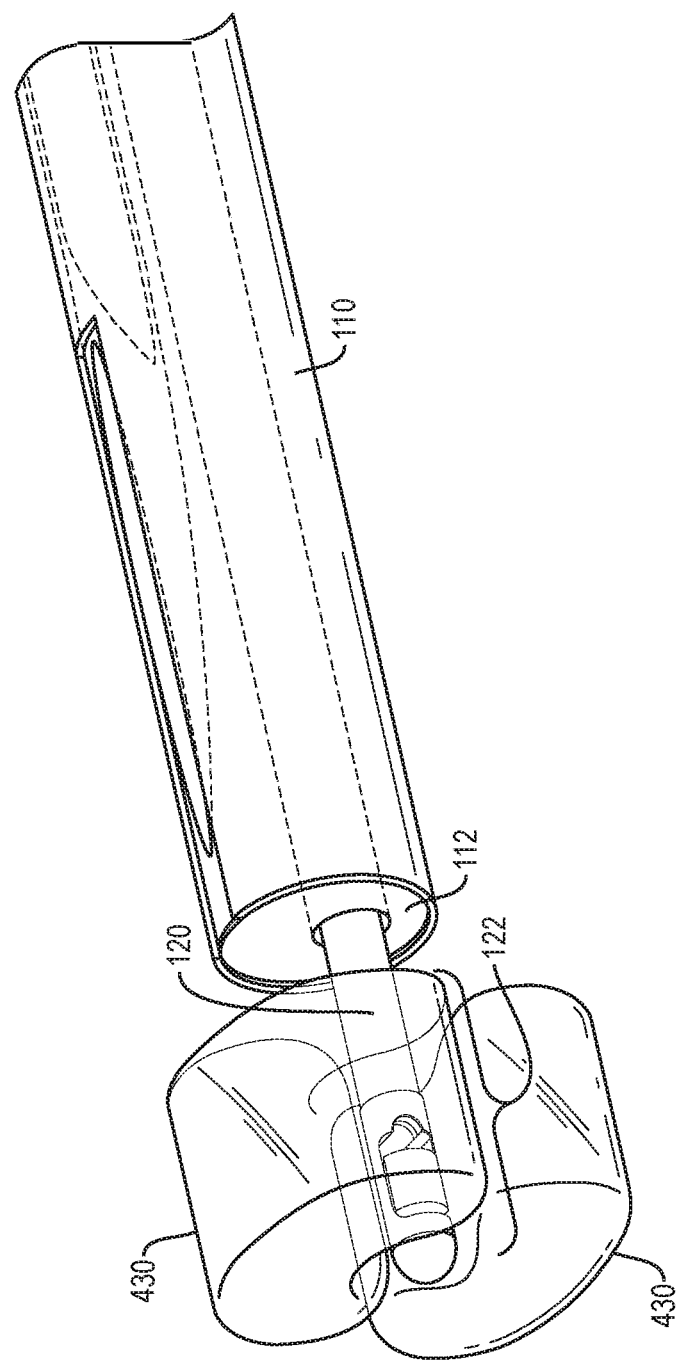

Referring to FIGS. 4A-4B, in one embodiment, a tissue biopsy system of the present disclosure may include two or more (compliant, semi-compliant or non-compliant) endcaps 430 attached to the distal portion 122 of the ultrasound probe 120. The endcaps 430 may provide additional structural support to the distal portion 122 of the ultrasound probe 120 when in the first configuration (FIG. 4A) as compared to single endcap, such as configuration of FIG. 3A. In addition, each of the endcaps 430 may include a separate/dedicated fluid delivery lumens (not shown) such that each endcap is able to move independently between the first and second configurations as necessary to maintain full circumferential contact with irregular or unevenly shaped body passages. For example, inflation fluid may flow between the external fluid source and the interior regions of the endcaps 430 through a separate dedicated fluid delivery lumen (not shown) extending along or through the ultrasound probe 120.

In use and by way of example, the biopsy systems disclosed herein may be advanced into a body passage (e.g., pulmonary peripheries) such that the endcap(s) 130, 230, 330, 430 is/are placed in radial (e.g., 360 degree) contact with the tissue wall of the body passage. Upon identification of a target tissue within or adjacent to the tissue wall, the tissue sampling element 150 may be distally advanced along ramped surface 118 of the second working channel 116 such that the tissue sampling element 150 deflects (e.g., bends) away from a longitudinal axis of the elongate member 110 and into the target tissue without contacting the endcap(s) 130, 230, 330, 430. The biopsy system may then be removed from the body passage and the target tissue captured within the lumen of the tissue sampling element 150 be removed for analysis. Alternatively, the tissue sampling element 150 may be proximally retracted along the ramped surface 118 of the second working channel 116, and the biopsy system advanced through the body passage to one or more additional target tissue sites, and the tissue sampling element 150 distally advanced to capture additional target tissue for analysis.

Although the end caps of the present disclosure have been described with respect to the specific embodiments illustrated in FIGS. 1A-4B, various embodiments, the disclosed tissue biopsy system may include any number of compliant, semi-compliant or non-compliant endcaps attached symmetrically or asymmetrically to the distal end 112 of the elongate member 110, or the distal portion 122 of the ultrasound probe 120. An inner or outer surface of an end cap, such as any of the disclosed endcaps 230, 330, 430, may include one or more pressure sensors to ensure that the endcap does not over-expand and cause distention of the pulmonary passage. Similarly, the endcap 130 of FIGS. 1A-1B may include one or more pressure sensors to ensure that undue force is not exerted against the tissue wall as the tissue biopsy system is advanced into the pulmonary peripheries. In addition to providing improved visualization of the pulmonary passages, any of the disclosed endcap configurations 130, 230, 330, 430 may provide a further benefit by securing and/or immobilizing the tissue biopsy system within the body passage such that longitudinal and/or rotational movement is minimized as the tissue sampling element is actuated, thereby reducing the likelihood of the tissue sampling element missing the target tissue. An additional benefit of any of the disclosed endcap configurations is the ability to place a portion of the pulmonary passage adjacent to the target tissue under tension such that the target tissue is at least partially immobilized for more precise/accurate biopsy by the tissue sampling element.

The medical devices of the present disclosure are not limited to bronchoscopes, and may include a variety of medical devices for accessing body passageways, including, for example, catheters, ureteroscopes, duodenoscopes, colonoscopes, arthroscopes, cystoscopes, hysteroscopes, and the like. Finally, although the embodiments of the present disclosure have been described in use with a bronchoscope, the tissue biopsy system of the present disclosure may be positioned within the patient in the absence of an accompanying medical device.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system, comprising:
an elongate member, comprising first and second working channels defining respective first and second openings;
an ultrasound probe disposed within the first working channel, wherein a distal portion of the ultrasound probe is extendable distally beyond a distal end of the elongate member; and
an endcap attached to the distal end of the elongate member to enclose and support the distal portion of the ultrasound probe when the probe is extended outside of the first opening,
wherein the second opening of the second working channel is orthogonal to a longitudinal axis of the elongate member and the longitudinal axis extends through the first opening of the first working channel, and
wherein the second working channel defines a ramped surface at the second opening within a distal portion of the elongate member, the ramped surface configured to deflect a tool extended out of the second opening away from the longitudinal axis of the elongate member without contacting the endcap.

2. The system of claim 1, further comprising a tissue sampling element slidably disposed within the second working channel.

3. The system of claim 1, wherein the first working channel extends between a proximal end and the distal end of the elongate member to define the first opening.

4. The system of claim 1, wherein the second working channel extends between a proximal end of the elongate member and an outer surface of the elongate member to define the second opening.

5. The system of claim 1, wherein the endcap comprises a hard plastic material.

6. The system of claim 1, wherein the endcap is filled with a conductive material.

7. The system of claim 1, wherein the endcap comprises an expandable member configured to move between a first configuration and a second configuration.

8. The system of claim 7, wherein the expandable member is moveable from the first configuration to the second configuration by flowing an inflation fluid into an interior region of the expandable member.

9. The system of claim 8, wherein the expandable member is moveable from the second configuration to the first configuration by flowing the inflation fluid out of the interior region of the expandable member.

10. The system of claim 1, wherein the endcap is attached to a circumference of the distal end of the elongate member.

11. The system of claim 1, wherein the endcap is attached about the first opening of the distal end of the elongate member.

12. A system, comprising:
an elongate member, comprising first and second working channels defining respective first and second openings;
an ultrasound probe disposed within the first working channel, wherein a distal portion of the ultrasound probe is extendable distally beyond a distal end of the elongate member; and
an endcap surrounding and supporting the distal portion of the ultrasound probe when the distal portion is extended distally beyond the distal end of the elongate member,
wherein the second opening of the second working channel is orthogonal to a longitudinal axis of the elongate member and the longitudinal axis extends through the first opening of the first working channel, and
wherein the second working channel defines a ramped surface at the second opening within a distal portion of the elongate member, the ramped surface configured to deflect a tool extended out of the second opening away from the longitudinal axis of the elongate member without contacting the endcap.

13. The system of claim 12, wherein the first working channel extends between a proximal end and the distal end of the elongate member to define the first opening.

14. The system of claim 12, wherein the second working channel extends between a proximal end of the elongate member and an outer surface of the elongate member to define the second opening.

15. The system of claim 12, wherein the endcap comprises an expandable member configured to move between a first configuration and a second configuration.

16. The system of claim 12, wherein the endcap is attached to a circumference of the distal end of the elongate member.

17. The system of claim 12, wherein the ultrasound probe comprises a radial ultrasound probe.

* * * * *